US012337116B2

(12) United States Patent
Montgomery et al.

(10) Patent No.: US 12,337,116 B2
(45) Date of Patent: Jun. 24, 2025

(54) DEVICES AND METHODS FOR ENGAGING INDEXED VALVE AND PRESSURIZED CANISTER ASSEMBLY WITH COLLAR AND FOR LINEAR ACTUATION BY PLUNGER ASSEMBLY INTO FLUID COMMUNICATION WITH DEVICE FOR REGULATING DRUG DELIVERY

(71) Applicant: Mallinckrodt Hospital Products IP Unlimited Company, Mulhuddart (IE)

(72) Inventors: Frederick J. Montgomery, Sun Prairie, WI (US); Duncan P. Bathe, Fitchburg, WI (US); Daniel J. Lee, Fremont, CA (US); Scott I. Biba, Madison, WI (US); Todd J. Bakken, Madison, WI (US)

(73) Assignee: Mallinckrodt Hospital Products IP Unlimited Company, Mulhuddart (IE)

( * ) Notice: Subject to any disclaimer, the term of this patent is extended or adjusted under 35 U.S.C. 154(b) by 0 days.

(21) Appl. No.: 18/368,769

(22) Filed: Sep. 15, 2023

(65) Prior Publication Data
US 2024/0017035 A1    Jan. 18, 2024

Related U.S. Application Data

(63) Continuation of application No. 17/509,556, filed on Oct. 25, 2021, now abandoned, which is a
(Continued)

(51) Int. Cl.
*A61M 16/14*    (2006.01)
*A61B 90/90*    (2016.01)
(Continued)

(52) U.S. Cl.
CPC ............. *A61M 16/14* (2013.01); *A61B 90/90* (2016.02); *A61B 90/94* (2016.02); *A61B 90/98* (2016.02); *A61M 16/12* (2013.01); *A61M 16/20* (2013.01); *A61M 16/209* (2014.02); *F17C 13/003* (2013.01); *F17C 13/04* (2013.01);
(Continued)

(58) Field of Classification Search
CPC ...... A61M 16/12; A61M 16/14; A61M 16/20; A61M 16/209; A61M 2209/0275; A61M 2205/6045; A61M 2205/6054; F17C 13/003; F17C 13/04; F17C 13/084; F17C 2205/0382; F17C 2223/0123;
(Continued)

(56) References Cited

U.S. PATENT DOCUMENTS

5,823,180 A * 10/1998 Zapol ................ A61M 15/0086
128/200.14
6,959,708 B1 * 11/2005 Rasor .................... A61M 37/00
604/24
(Continued)

*Primary Examiner* — Valerie L Woodward
(74) *Attorney, Agent, or Firm* — SERVILLA WHITNEY LLC (57) ABSTRACT

A valve assembly including a housing and a valve, the valve being disposed within the housing, a first indexed member integral to the housing, the first indexed member adapted to be complementary to a second indexed member, and a radio frequency identification device adapted to communicate with a radio frequency receiver, the valve being configured to align with a canister, seal the canister and open in a single movement. A drug containment device having said valve assembly is also disclosed.

9 Claims, 7 Drawing Sheets

Related U.S. Application Data continuation of application No. 15/899,063, filed on Feb. 19, 2018, now Pat. No. 11,154,684, which is a continuation of application No. 14/301,692, filed on Jun. 11, 2014, now Pat. No. 9,895,199, which is a continuation of application No. 13/260,505, filed as application No. PCT/US2009/045266 on May 27, 2009, now Pat. No. 8,757,148.

(51) Int. Cl.

| | | |
|---|---|---|
| *A61B 90/94* | (2016.01) | |
| *A61B 90/98* | (2016.01) | |
| *A61M 16/12* | (2006.01) | |
| *A61M 16/20* | (2006.01) | |
| *F17C 13/00* | (2006.01) | |
| *F17C 13/04* | (2006.01) | |

(52) U.S. Cl.
CPC ............... *A61M 2202/0208* (2013.01); *A61M 2202/0233* (2013.01); *A61M 2202/0266* (2013.01); *A61M 2202/0275* (2013.01); *A61M 2205/6045* (2013.01); *A61M 2205/6054* (2013.01); *F17C 2201/0104* (2013.01); *F17C 2201/0109* (2013.01); *F17C 2201/032* (2013.01); *F17C 2201/058* (2013.01); *F17C 2205/0153* (2013.01); *F17C 2205/0188* (2013.01); *F17C 2205/0323* (2013.01); *F17C 2205/0382* (2013.01); *F17C 2205/058* (2013.01); *F17C 2221/014* (2013.01); *F17C 2221/031* (2013.01); *F17C 2223/0123* (2013.01); *F17C 2223/013* (2013.01); *F17C 2260/028* (2013.01); *F17C 2270/02* (2013.01); *F17C 2270/025* (2013.01)

(58) Field of Classification Search
CPC ........ F17C 2203/018; F17C 2205/0188; F17C 2205/0153; A61B 90/90
See application file for complete search history.

(56) References Cited

U.S. PATENT DOCUMENTS

| | | | |
|---|---|---|---|
| 6,981,612 B2* | 1/2006 | Siimes | F16K 1/303 |
| | | | 251/149.6 |
| 2009/0071481 A1* | 3/2009 | Fishman | A61M 16/024 |
| | | | 128/204.18 |
| 2009/0301581 A1* | 12/2009 | MacNeal | F16K 27/08 |
| | | | 137/530 |

* cited by examiner

DEVICES AND METHODS FOR ENGAGING INDEXED VALVE AND PRESSURIZED CANISTER ASSEMBLY WITH COLLAR AND FOR LINEAR ACTUATION BY PLUNGER ASSEMBLY INTO FLUID COMMUNICATION WITH DEVICE FOR REGULATING DRUG DELIVERY

CROSS-REFERENCE TO RELATED APPLICATIONS

This application is a continuation application of U.S. patent application Ser. No. 17/509,556, filed on Oct. 25, 2021, which is continuation application of U.S. patent application Ser. No. 15/899,063, filed on Feb. 19, 2018, now U.S. Pat. No. 11,154,684, which is a continuation application of U.S. patent application Ser. No. 14/301,692, filed on Jun. 11, 2014, now U.S. Pat. No. 9,895,199, which is a continuation application of U.S. patent application Ser. No. 13/260,505, filed Sep. 26, 2011, now U.S. Pat. No. 8,757, 148, which is the National Phase entry of PCT/US2009/045266, filed May 27, 2009, the entire content of which are incorporated herein by reference in their entirety.

STATEMENT CONCERNING FEDERALLY SPONSORED RESEARCH OR DEVELOPMENT

Not Applicable.

BACKGROUND OF THE INVENTION

Various keying and canister or cylinder actuation devices are known. In the technology concerning the inhalation of drugs from pressurized cylinders, the cylinders have been large and not easily portable. The cylinders are also unprotected to the surrounding hospital environment, which can be physically rigorous. The connection between the cylinder and the regulation device can be cumbersome.

Perhaps the most significant drawback, however, is the risk of connecting a cylinder containing an inappropriate, wrong or otherwise unsuitable drug and/or dosing concentration to the regulation device.

Hence, devices that provide improved connection of the cylinder to the regulation device, improved protection of the cylinder, enhanced portability of the cylinder, and, means for ensuring that a cylinder containing the correct drug and dosing concentration is connected to the drug delivery and regulation device would be advantageous.

SUMMARY OF THE INVENTION

One aspect of the invention is an indexed valve assembly comprising a housing and a valve, the valve disposed within the housing, and, a first indexed member integral to the housing, the first indexed member adapted to be complementary to a second indexed member.

In an exemplary embodiment of the indexed valve assembly, the assembly further comprises a third indexed member integral to the housing, the third indexed member adapted to be complementary to a fourth indexed member, the first indexed member is non-complementary to the fourth indexed member, and, the third indexed member is non-complementary to the second indexed member.

In another exemplary embodiment of the indexed valve assembly, the assembly further comprises a plurality of indexed members, each indexed member adapted to be complementary to a corresponding indexed member and non-complementary to a non-corresponding indexed member.

In another exemplary embodiment of the indexed valve assembly, one or more indexed members are predeterminately adapted to indicate the identity and canister concentration of an active pharmaceutical ingredient (API).

In another exemplary embodiment of the indexed valve assembly, the API comprises nitric oxide, and, the canister concentration is in the range of approximately 50 ppm or 100 ppm to 800 ppm, 2400 ppm, 2500 ppm or 10,000 ppm. The concentrations herein may also be expressed in mg/L, whereby the conversion is approximately 12 mg/L per 10,000 ppm.

In another exemplary embodiment of the indexed valve assembly, the indexed members are further predeterminately adapted to indicate an initial volume of approximately 32 L of compressible gas or 0.16 L of liquid.

In another exemplary embodiment of the indexed valve assembly, the API comprises carbon monoxide, and, the canister concentration is in the range of approximately 500 ppm or 3000 ppm to 5000 ppm, 10,000 ppm, 15,000 ppm or 20,000 ppm.

In another exemplary embodiment of the indexed valve assembly, the API comprises a chalcogenide compound.

In another exemplary embodiment of the indexed valve assembly, the valve is a spring-biased needle valve.

In another exemplary embodiment of the indexed valve assembly, the first indexed member or second indexed member is a key.

In another exemplary embodiment of the indexed valve assembly, the key is a tongue, prong, post, ridge, protrusion or rail.

In another exemplary embodiment of the indexed valve assembly, the first indexed member or second indexed member is an opening.

In another exemplary embodiment of the indexed valve assembly, the opening is a groove, slot, channel, aperture or hole.

In another exemplary embodiment of the indexed valve assembly, the first indexed member is an opening, the second indexed member is a key, the third indexed member is an opening, and, the fourth indexed member is a key.

In another exemplary embodiment of the indexed valve assembly, the first indexed member is a slot, the second indexed member is rail, the third indexed member is a slot, and, the fourth indexed member is a rail.

Another aspect of the invention is an indexed drug containment device for inhalation comprising a valve assembly comprising a housing and a valve, the valve disposed within the housing, a first indexed member integral to the housing, the first indexed member adapted to be complementary to a second indexed member, and, a canister in fluid communication with the valve assembly, the canister containing an API and a inactive carrier gas.

In an exemplary embodiment of the indexed drug containment device, the device further comprises a third indexed member integral to the housing, the third indexed member adapted to be complementary to a fourth indexed member, the first indexed member is non-complementary to the fourth indexed member, and, the third indexed member is non-complementary to the second indexed member.

In another exemplary embodiment of the indexed drug containment device, the device further comprises a plurality of indexed members, each indexed member adapted to be complementary to a corresponding indexed member and non-complementary to a non-corresponding indexed member.

In another exemplary embodiment of the indexed drug containment device, one or more indexed members are predeterminately adapted to indicate the identity and canister concentration of the API.

In another exemplary embodiment of the indexed drug containment device, the API comprises nitric oxide, the inactive carrier gas comprises nitrogen gas ($N_2$), and, the canister concentration is in the range of approximately 50 ppm or 100 ppm to 800 ppm, 2400 ppm, 2500 ppm or 10,000 ppm.

In another exemplary embodiment of the indexed drug containment device, the indexed members are further predeterminately adapted to indicate an initial volume of approximately 32 L of compressible gas or 0.16 L of liquid.

In another exemplary embodiment of the indexed drug containment device, the API comprises carbon monoxide, the inactive carrier gas comprises oxygen gas ($O_2$) and, optionally, the balance comprising $N_2$, and, the canister concentration is in the range of approximately 500 ppm or 3000 ppm to 5000 ppm, 10,000 ppm, 15,000 ppm or 20,000 ppm.

In another exemplary embodiment, the carrier gas comprises around 30% $O_2$ and 70% $N_2$.

In another exemplary embodiment of the indexed drug containment device, the API comprises a chalcogenide compound at a suitable concentration.

In another exemplary embodiment of the indexed drug containment device, the valve is a spring-biased needle valve.

In another exemplary embodiment of the indexed drug containment device, the first indexed member or second indexed member is a key.

In another exemplary embodiment of the indexed drug containment device, the key is a tongue, prong, post, ridge, protrusion or rail.

In another exemplary embodiment of the indexed drug containment device, the first indexed member or second indexed member is an opening.

In another exemplary embodiment of the indexed drug containment device, the opening is a groove, slot, channel, aperture or hole.

In another exemplary embodiment of the indexed drug containment device, the first indexed member is an opening, the second indexed member is a key, the third indexed member is an opening, and, the fourth indexed member is a key.

In another exemplary embodiment of the indexed drug containment device, the first indexed member is a slot, the second indexed member is rail, the third indexed member is a slot, and, the fourth indexed member is a rail.

Another aspect of the invention is an indexed drug actuation device comprising a valve assembly comprising a housing and a valve, the valve disposed within the housing, a first indexed member integral to the housing, the first indexed member adapted to be complementary to a second indexed member, a canister in fluid communication with the valve assembly, the canister containing an API and a inactive carrier gas, and, a collar comprising the second indexed member, the second indexed member integral to the collar.

In an exemplary embodiment of the indexed drug actuation device, the device further comprises a third indexed member integral to the housing and a fourth indexed member integral to the collar, the third indexed member adapted to be complementary to the fourth indexed member, the first indexed member is non-complementary to the fourth indexed member, and, the third indexed member is non-complementary to the second indexed member.

In an exemplary embodiment of the indexed drug actuation device, the device further comprises a plurality of indexed members, each indexed member adapted to be complementary to a corresponding indexed member and non-complementary to a non-corresponding indexed member.

In another exemplary embodiment of the indexed drug actuation device, one or more indexed members are predeterminately adapted to indicate the identity and canister concentration of the API.

In another exemplary embodiment of the indexed drug actuation device, the API comprises nitric oxide, the inactive carrier gas comprises $N_2$ and, the canister concentration is in the range of approximately 50 ppm or 100 ppm to 800 ppm, 2400 ppm, 2500 ppm or 10,000 ppm.

In another exemplary embodiment of the indexed drug actuation device, the indexed members are further predeterminately adapted to indicate an initial volume of approximately 32 L of compressible gas or 0.16 L of liquid.

In another exemplary embodiment of the indexed drug actuation device, the API comprises carbon monoxide, the inactive carrier gas comprises $O_2$ and, optionally the balance comprises $N_2$, and, the canister concentration is in the range of approximately 500 ppm or 3000 ppm to 5000 ppm, 10,000 ppm, 15,000 ppm or 20,000 ppm.

In another exemplary embodiment of the indexed drug actuation device, the API comprises a chalcogenide compound.

In another exemplary embodiment of the indexed drug actuation device, the valve is a spring-biased needle valve.

In another exemplary embodiment of the indexed drug actuation device, the first indexed member or second indexed member is a key.

In another exemplary embodiment of the indexed drug actuation device, the key is a tongue, prong, post, ridge, protrusion or rail.

In another exemplary embodiment of the indexed drug actuation device, the first indexed member or second indexed member is an opening.

In another exemplary embodiment of the indexed drug actuation device, the opening is a groove, slot, channel, aperture or hole.

In another exemplary embodiment of the indexed drug actuation device, the first indexed member is an opening, the second indexed member is a key, the third indexed member is an opening, and, the fourth indexed member is a key.

In another exemplary embodiment of the indexed drug actuation device, the first indexed member is a slot, the second indexed member is rail, the third indexed member is a slot, and, the fourth indexed member is a rail.

Another aspect of the invention is an indexed drug delivery device comprising a valve assembly comprising a housing and a valve, the valve disposed within the housing, a first indexed member integral to the housing, the first indexed member adapted to be complementary to a second indexed member, a canister in fluid communication with the valve assembly, the canister containing an active pharmaceutical ingredient and an inactive carrier gas, a collar comprising the second indexed member, the second indexed member integral to the collar, a receiving assembly comprising a receptacle adapted to engage at least a portion of the housing, and, a seat adapted to engage the valve, and, a plunger assembly adapted to linearly actuate the valve assembly and canister along an axis and to engage the valve and seat, the plunger assembly comprising a carriage fixed to the collar, and, a lever having a cam adapted to engage a spring, the spring adapted to linearly actuate the carriage, valve assembly, canister and collar along the axis.

In an exemplary embodiment of the indexed drug delivery device, the device further comprises a third indexed member integral to the housing and a fourth indexed member integral to the collar, the third indexed member adapted to be complementary to the fourth indexed member, the first indexed member is non-complementary to the fourth indexed member, and, the third indexed member is non-complementary to the second indexed member.

In another exemplary embodiment of the indexed drug delivery device, the device further comprises a plurality of indexed members, each indexed member adapted to be complementary to a corresponding indexed member and non-complementary to a non-corresponding indexed member.

In another exemplary embodiment of the indexed drug delivery device, one or more indexed members are predeterminately adapted to indicate the identity and canister concentration of the API.

In another exemplary embodiment of the indexed drug delivery device, the API comprises nitric oxide, the carrier gas comprises $N_2$ and, the canister concentration is in the range of approximately 50 ppm or 100 ppm to 800 ppm, 2400 ppm, 2500 ppm or 10,000 ppm.

In another exemplary embodiment of the indexed drug delivery device, the indexed members are further predeterminately adapted to indicate an initial volume of approximately 32 L of compressible gas or 0.16 L of liquid.

In another exemplary embodiment of the indexed drug delivery device, the API comprises carbon monoxide, the inactive carrier gas comprises $O_2$ and, optionally the balance comprises $N_2$, and, the canister concentration is in the range of approximately 500 ppm or 3000 ppm to 5000 ppm, 10,000 ppm, 15,000 ppm or 20,000 ppm.

In another exemplary embodiment of the indexed drug delivery device, the API comprises a chalcogenide compound.

In another exemplary embodiment of the indexed drug delivery device, the valve is a spring-biased needle valve.

In another exemplary embodiment of the indexed drug delivery device, the first indexed member or second indexed member is a key.

In another exemplary embodiment of the indexed drug delivery device, the key is a tongue, prong, post, ridge, protrusion or rail.

In another exemplary embodiment of the indexed drug delivery device, the first indexed member or second indexed member is an opening.

In another exemplary embodiment of the indexed drug delivery device, the opening is a groove, slot, channel, aperture or hole.

In another exemplary embodiment of the indexed drug delivery device, the first indexed member is an opening, the second indexed member is a key, the third indexed member is an opening, and, the fourth indexed member is a key.

In another exemplary embodiment of the indexed drug delivery device, the first indexed member is a slot, the second indexed member is rail, the third indexed member is a slot, and, the fourth indexed member is a rail.

In another exemplary embodiment of the indexed drug delivery device, the cam is adapted to engage a compression spring, and, the compression spring is adapted to engage the carriage.

Another aspect of the invention is a valve assembly comprising a housing and a valve, the valve disposed within the housing, and, a radio frequency identification device adapted to communicate with a radio frequency receiver.

Another aspect of the invention is a pressurized drug containment device for inhalation comprising a valve assembly comprising a housing and a valve, the valve disposed within the housing, a radio frequency identification device adapted to communicate with a radio frequency receiver, and, a canister in fluid communication with the valve assembly, the canister containing an API and a inactive carrier gas.

Another aspect is a method of engaging the above pressurized drug-containing canister comprising linearly actuating along an axis the above drug containment device to engage a receptacle and to engage the valve with a seat.

Another aspect of the invention is a method of engaging a pressurized canister comprising linearly actuating along an axis an indexed drug-containing pressurized canister to engage a receptacle and to engage the valve with a seat.

Another aspect of the invention is a method of engaging a pressurized canister comprising linearly actuating along an axis an indexed pressurized canister to engage a receptacle and to engage the valve with a seat.

Another aspect of the invention is a drug delivery device for regulating delivery of an API to a patient comprising a valve assembly comprising a housing and a valve, the valve disposed within the housing, a first indexed member integral to the housing, the first indexed member adapted to be complementary to a second indexed member, a canister in fluid communication with the valve assembly, the canister containing the API and an inactive carrier gas, a collar comprising the second indexed member, the second indexed member integral to the collar, a receiving assembly comprising a receptacle adapted to engage at least a portion of the housing, and, a seat adapted to engage the valve, a plunger assembly adapted to linearly actuate the valve assembly and canister along an axis and to engage the valve and seat, the plunger assembly comprising a carriage fixed to the collar, and, a lever having a cam adapted to engage a spring, the spring adapted to linearly actuate the carriage, valve assembly, canister and collar along the axis, and, a controllable drug delivery and regulation device adapted to regulate the delivery of the API to the patient.

In an exemplary embodiment of the drug delivery device, the device further comprises a third indexed member integral to the housing and a fourth indexed member integral to the collar, the third indexed member adapted to be complementary to the fourth indexed member, the first indexed member is non-complementary to the fourth indexed member, and, the third indexed member is non-complementary to the second indexed member.

In another exemplary embodiment of the drug delivery device, the device further comprises a plurality of indexed members, each indexed member adapted to be complementary to a corresponding indexed member and non-complementary to a non-corresponding indexed member.

In another exemplary embodiment of the drug delivery device, one or more indexed members are predeterminately adapted to indicate the identity and canister concentration of the API.

In another exemplary embodiment of the drug delivery device, the API comprises nitric oxide, the inactive carrier gas comprises $N_2$, and, the canister concentration is in the range of approximately 50 ppm or 100 ppm to 800 ppm, 2400 ppm, 2500 ppm or 10,000 ppm.

In another exemplary embodiment of the drug delivery device, the indexed members are further predeterminately adapted to indicate an initial volume of approximately 32 L of compressible gas or 0.16 L of liquid.

In another exemplary embodiment of the drug delivery device, the API comprises carbon monoxide, the inactive carrier gas comprises $O_2$ and, optionally a balance comprising $N_2$, and, the canister concentration is in the range of approximately 500 ppm or 3000 ppm to 5000 ppm, 10,000 ppm, 15,000 ppm or 20,000 ppm.

In another exemplary embodiment of the drug delivery device, the API comprises a chalcogenide compound.

In another exemplary embodiment of the drug delivery device, the valve is a spring-biased needle valve.

In another exemplary embodiment of the drug delivery device, the first indexed member or second indexed member is a key.

In another exemplary embodiment of the drug delivery device, the key is a tongue, prong, post, ridge, protrusion or rail.

In another exemplary embodiment of the drug delivery device, the first indexed member or second indexed member is an opening.

In another exemplary embodiment of the drug delivery device, the opening is a groove, slot, channel, aperture or hole.

In another exemplary embodiment of the drug delivery device, the first indexed member is an opening, the second indexed member is a key, the third indexed member is an opening, and, the fourth indexed member is a key.

In another exemplary embodiment of the drug delivery device, the first indexed member is a slot, the second indexed member is rail, the third indexed member is a slot, and, wherein the indexed member is a rail.

In another exemplary embodiment of the drug delivery device, the cam is adapted to engage a compression spring, and, the compression spring is adapted to engage the carriage.

Another aspect of the invention is a method of producing pulmonary vasodilation in a patient in need thereof comprising providing any of the above drug delivery devices for delivering nitric oxide, and, delivering a controlled and regulated pharmaceutical dose or dose rate of nitric oxide to the patient.

Another aspect of the invention is a method of treating a disease or disorder selected from the group consisting of outcomes in organ transplant, delayed graph function associated with organ transplant, cystic fibrosis, ileus, necrotizing enterocolitis, vascular restenosis, hepatitis, acute liver failure associated with hepatitis and hemorrhagic shock, in a patient in need thereof comprising providing any of the above drug delivery devices for delivering a controlled and regulated pharmaceutical dose or dose rate of carbon monoxide to the patient.

Another aspect of the invention is a drug delivery device for regulating delivery of an API to a patient comprising a receiving assembly comprising a receptacle adapted to engage at least a portion of an indexed drug containment device, a seat adapted to engage the valve of the indexed drug containment device, a plunger assembly adapted to linearly actuate the valve assembly and canister along an axis and to engage the valve and seat, the plunger assembly comprising a carriage fixed to the collar, and, a lever having a cam adapted to engage a spring, the spring adapted to linearly actuate the carriage, valve assembly, canister and collar along the axis, and, a controllable drug delivery and regulation device adapted to regulate the delivery of the API to the patient.

BRIEF DESCRIPTION OF THE EXEMPLARY EMBODIMENTS

FIG. 6 shows a partial sectional front view of the collar canister assembly positioned in a pressurized gas drug delivery device. FIG. 6 also shows a cover and a lever of the delivery device in an open position.

FIG. 7 shows a partial sectional front view of the collar canister assembly positioned in the pressurized gas drug delivery device. FIG. 7 also shows the cover and the lever of the delivery device in an operating position.

DETAILED DESCRIPTION OF THE EXEMPLARY EMBODIMENTS

The embodiments and aspects of the invention, as described herein, may be used to deliver a medical pharmaceutical gas to a patient in need of treatment for multiple diseases or disorders. For example, the drug delivery devices, as described herein may be used to deliver nitric oxide to a patient for the treatment of reversible pulmonary hypertension as described in U.S. Pat. Nos. ("USPN's") 5,873,359 and 5,485,827; or, sickle cell disease as described in U.S. Pat. No. 5,885,621, all of which are incorporated herein by reference in their entirety.

In addition, the drug delivery devices, as described herein may be used to deliver carbon monoxide to a patient for the treatment of the following: Organ transplant outcomes as described in U.S. patent application Ser. No. ("USSN") 11/401,722 (US 2007/02020083); cystic fibrosis as described in U.S. Ser. No. 10/053,535 (US 2002/0155166); ileus as described in U.S. Ser. No. 10/371,666 (US 2003/0219497); necrotizing enterocolitis as described in U.S. Ser. No. 10/413,817 (US 2004/0005367); vascular disease including vascular restenosis as described in U.S. Ser. No. 10/367,277 (US 2003/0219496) and Ser. No. 12/050,826 (US 2008/0167609); or, hepatitis including acute liver failure as described in U.S. Ser. No. 10/439,632 (US 2004/0052866), all of which are incorporated herein by reference in their entirety.

As used herein, the term "key" (and variations thereof) means a structure adapted to engage a corresponding opening, such as a tongue, prong, post, rail, ridge or protrusion.

As such, as used herein, the term "opening" (and variations thereof) means a structure defined by one or more adjacent or surrounding structures that is adapted to engage a key, such as a slot, groove, channel, aperture or hole.

As used herein, the term "member" (and variations thereof) includes both keys and openings.

As used herein, the term "indexed" (and variations thereof) means that one or more members are designed to predeterminately indicate the identity and/or dosing concentration of the API.

As used herein, the term "complementary" (and variations thereof) means that an indexed member and a corresponding indexed member engage to form an interface, whereby, upon engagement sufficient for actuation, the interface is flush.

As used herein, the term "non-complementary" (and variations thereof) means that two indexed members are not complementary.

As used herein, the term "interface" (and variations thereof) means the flush surfaces of two complementary indexed members.

Figure 1:
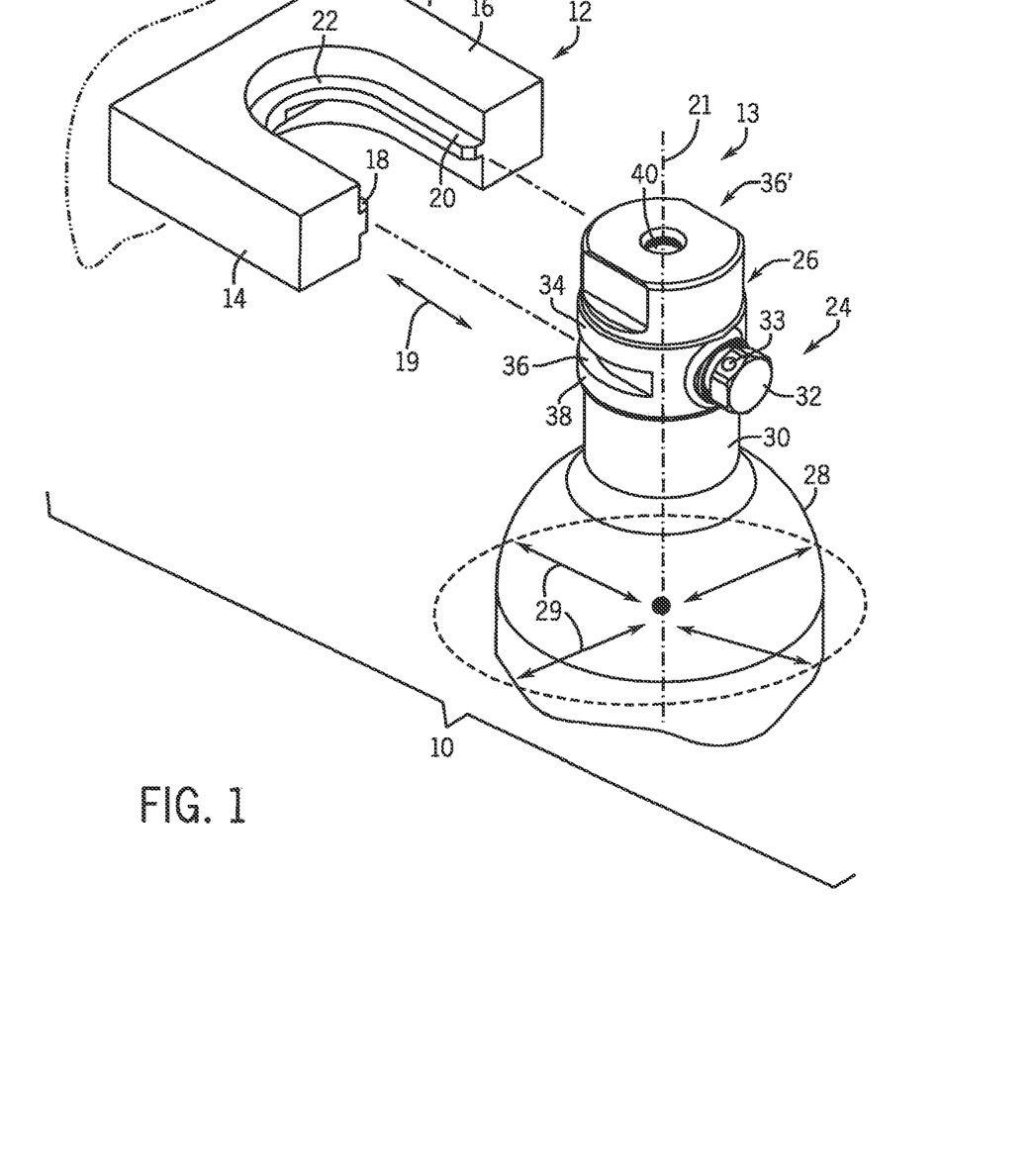
FIG. 1 shows a partial perspective view of the collar canister assembly.
Figure 8:
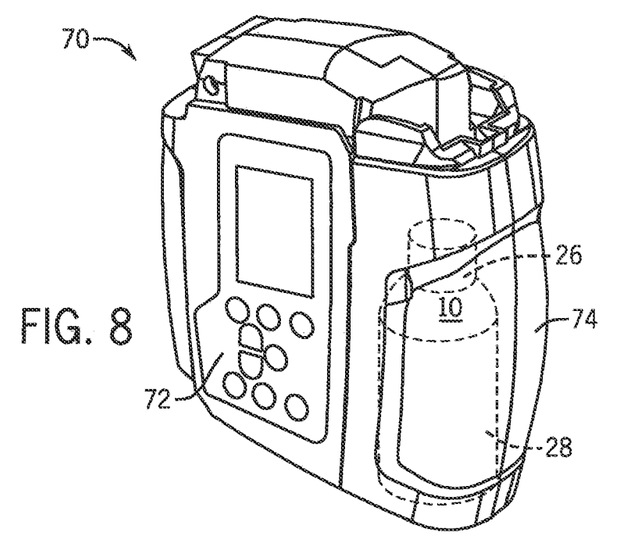
FIG. 8 is a perspective view of a pressurized gas drug delivery device including the collar canister assembly.

Shown in FIG. 1 is an indexed drug actuation device 10 for use in an indexed drug delivery and regulation device 70 (FIG. 8). The indexed drug actuation device 10 provides indexing features that permit specific drug delivery devices to dispense a predetermined concentration of an API contained in a pharmaceutically inactive carrier gas. The indexed device 10 includes a collar 12 and an indexed drug containment device 24. The device 24 includes an indexed valve assembly 13 threaded to a canister 28.

In an exemplary embodiment, the indexed device 10 contains 100 ppm or 800 ppm of nitric oxide in accordance with the current drug label insert for INOmax® (nitric oxide) for inhalation (SPC-0303 V:3.0), which is incorporated herein by reference in its entirety. It may also be used in connection with other formulations of INOmax® at higher concentrations such as 2400 ppm of nitric oxide. For example, the indexing features may permit only engagement of the device 10 containing nitric oxide and/or a specific concentration of nitric oxide.

The API may be carbon monoxide, nitric oxide, or a chalcogenide compound. The API concentration may be any concentration within the range of 100 ppm to 15,000 ppm. The inactive carrier gas may comprise $O_2$, $N_2$ and/or another pharmaceutically suitable inactive carrier gas. The canister 28 may have sufficient capacity to store 30 L to 35 L at a pressure in the range of 2000 psig to 3000 psig. Other sized canisters with different pressures and capacities may also be utilized.

As shown in FIG. 1, the indexed drug actuation device 10 includes a collar 12 configured to transversely engage a valve housing 26 of the indexed valve assembly 13. The collar 12 is generally U-shaped and includes a first arm 14 and a second arm 16. The collar 12 transversely engages the housing 26. The inner faces of the first arm 14 and the second arm 16 include a first collar key 18 and a second collar key 20, respectively. The first and second collar keys 18, 20 are elongated in a transverse direction 19 to provide rail structures.

As used herein, the term "transverse direction" (and variations thereof, such as "transversely") means a direction in which the indexed valve assembly 13 is engagable and removable from the collar 12, that is, perpendicular to the longitudinal axis 21.

As used herein, the term "longitudinal axis" (and variations thereof, such as simply "axial") means an axis longitudinally aligned with canister 28.

The first and second collar keys 18, 20 may differ in shape (such as cross-sectional shape, axial position, axial width, or orientation) to provide the indexing features and functionality. Other shapes, arrangements, configurations, and combinations of the collar keys 18, 20 are described in further detail below. The first and second collar keys 18, 20 also provide an arcuate key 22 between the first and second arms 14, 16, which may also provide indexing for API identification.

The sides of the valve housing 26 also include structures that engage the collar keys 18, 20. Specifically, one side of the valve housing 26 includes an upper key ridge 34 that extends outwardly in a radial direction 29 relative to a first valve opening 36 that accommodates the first collar key 18.

As used herein, the term "radial direction" (and variations thereof, such as "radial") means a direction perpendicular to the longitudinal axis 21.

The term "radially inwardly" (and variations thereof) means toward the longitudinal axis 21 in a radial direction.

The term "radially outwardly" (and variations thereof) means away from the longitudinal axis 21 in a radial direction.

The first valve opening 36 may also engage a portion of the arcuate key 22. This side of the valve housing 26 also includes a lower key ridge 38 longitudinally opposite the upper key ridge 34 that extends radially outwardly relative to the first valve opening 36.

Figure 3:
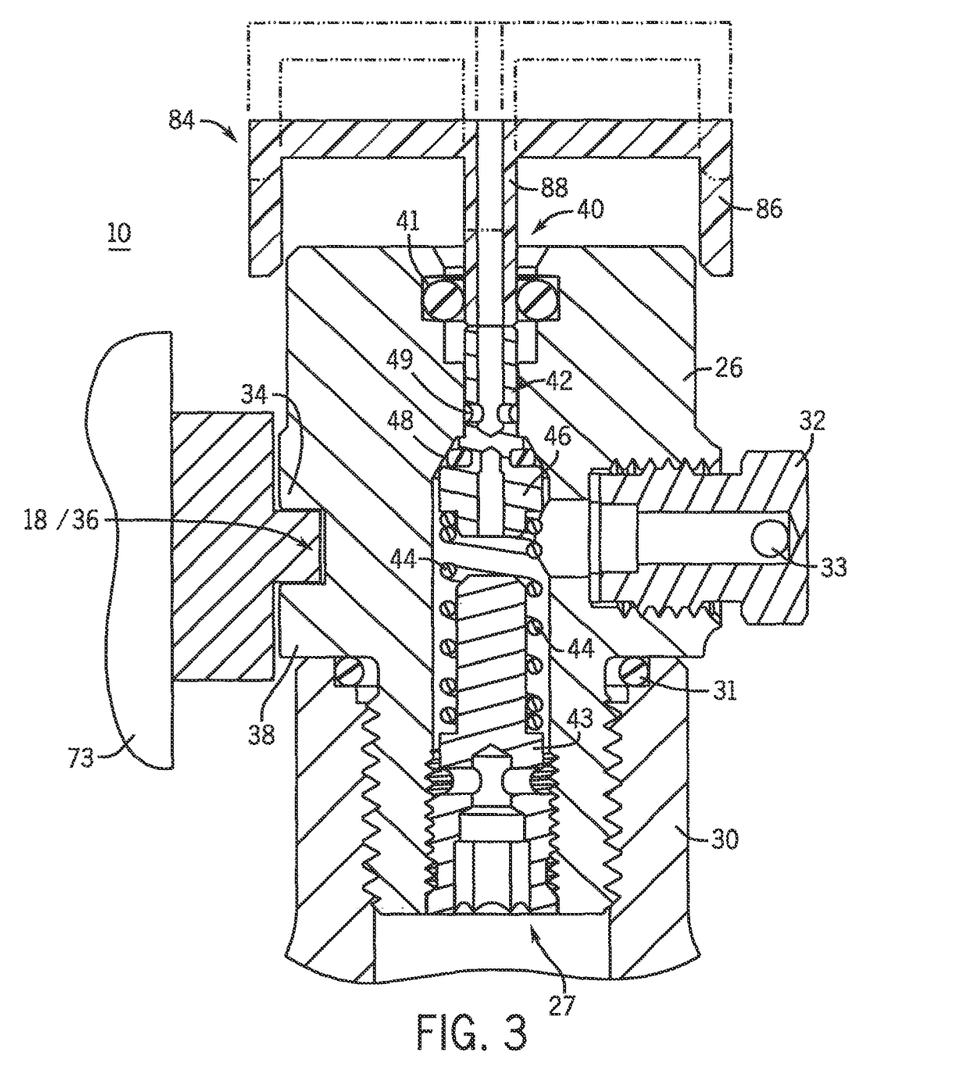
FIG. 3 shows a side sectional view of the collar canister assembly of FIG. 1 illustrating the receptacle before engaging the assembly.
Figure 4:
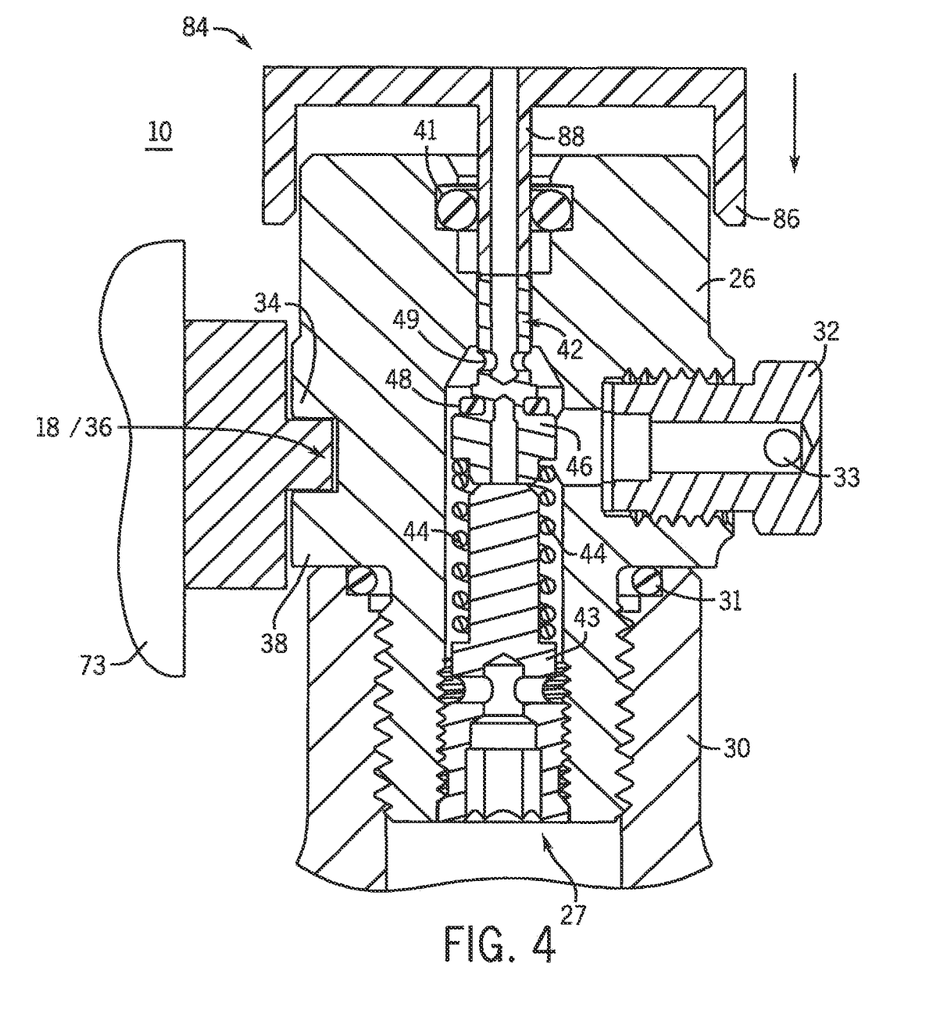
FIG. 4 shows a side sectional view of the collar canister assembly of FIG. 1 illustrating the receptacle engaging the assembly.

As shown in FIGS. 1, 3 and 4, the opposite side of the valve housing 26 also includes upper and lower key ridges 34, 38 that extend radially outwardly relative to a second valve opening 36'. The second valve opening 36' accommodates the second collar key 20. The valve openings 36, 36' are complementary to the collar keys 18, 20, respectively.

The valve openings 36, 36' and the collar keys 18, 20 have rectangular cross-sections. However, other cross-sectional shapes may be used, such as semi-circular, triangular, trapezoidal, pentagonal, an so on.

Alternatively, the cross-sectional shapes of the set of indexed members 18, 36 and 20/36' may differ from each other. For example, the indexed members 18, 36 may have rectangular cross-sections and the indexed members 20, 36' may have trapezoidal cross-sections. The cross-sectional shapes and/or other structural features of the sets of indexed members 18, 36 and 20, 36' provide the aforementioned indexing of the API and/or dosing concentration.

As a result, the indexed collar 12 engages only an indexed drug containment device 24, whereby the indexing provides fully complementary members identified for the predetermined API and/or dosing concentration. The cross-sectional shapes and/or other structural features of the sets of indexed members 18, 36 and 20, 36' may also provide for non-complementary indexed members on the collar 12 and the valve housing 26 when the valve housing is turned by 180 degrees relative to the collar 12. That is, the first collar key 18 is non-complementary with the second valve opening 36' and the second collar key 20 is non-complementary with the first valve opening 36 such that the canister 28 can only be inserted into the collar 12 one way. The relief valve 32 that includes a relief outlet 33 may also provide structure preventing incorrect engagement of the collar 12 and valve housing 26. Even without the relief valve 32 if the valve housing doesn't have an opening in the relief valve location that will allow the arcuate key of the collar to mate with the opening, it will not be possible for the valve housing to fully engage with the collar.

The valve housing 26 may also include additional keys and the collar 12 may include additional openings. The valve housing 26 and the collar 12 may each include one or more keys and one or more openings. The collar 12 may include different types of keys. The valve housing 26 may include different types of openings. For example, the collar 12 may include rails along the first and second arms 14, 16 and one or more posts instead of the arcuate key 22. The valve housing 26 may include slots that accommodate the rails and one or more apertures that accommodate the posts.

As shown in FIGS. 1, 3, and 4, the collar 12 engages the valve housing 26. The valve housing 26 includes a first end that defines an inlet 27. The valve housing 26 threadably engages the neck 30 of the canister 28. The canister 28 is aligned along longitudinal axis 21. Alternatively, the valve housing 26 may communicate with the canister 28 through a conduit or hose (not shown).

The connection between the valve housing 26 and the canister 28 also includes an o-ring 31 (see FIGS. 3 and 4) adapted to prevent leaking of API and carrier gas from the canister 28. The valve housing 26 also includes an optional relief valve 32 threaded into the valve housing 26. The relief valve 32 includes a relief outlet 33. The relief valve 32 may be any suitable valve known in the art that prevents overpressurization of the contents of the canister 28 due to for example high temperatures due to fire or overfilling of the canister during production.

Figure 2:
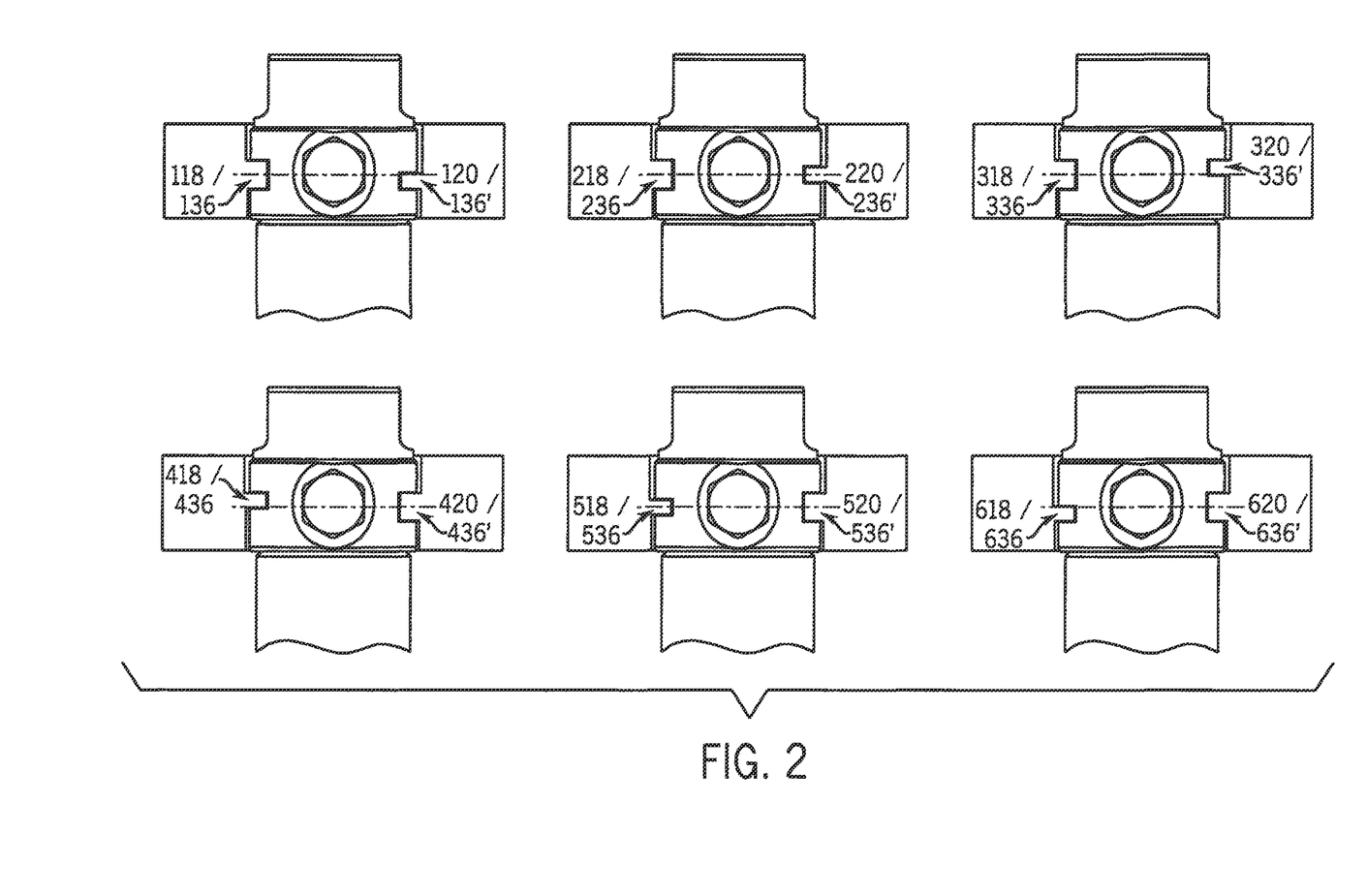
FIG. 2 shows several partial front views illustrating interfaces between the collar and the canister.

As shown in FIG. 2, the indexing features that correspond to the identity and/or dosing concentration of the API may be provided by one or more of different axial width, axial juxtaposition, different cross-sectional shape, and the like, of the interfaces 18/36 and 20/36'.

As used herein, the term "axial juxtaposition" means that the mid-planes of the interfaces 18/36 and 20/36' are offset (i.e., not in alignment).

As used herein, the term "mid-plane" (and variations thereof) means a plane perpendicular to the longitudinal axis that bisects an interface.

As used herein, the term "aligned" (and variations thereof such as "alignment") means that the mid-planes of two or more interfaces are coplanar.

As used herein, the term "offset" (and variations thereof) means that the mid-planes of two or more interfaces are not coplanar.

Several exemplary embodiments of the interfaces are shown in FIG. 2. In one embodiment, the second interface 120/136' has a smaller axial width than the first interface 118/136, and, the second interface 120/136' is also axially juxtaposed below the mid-plane of the first interface 118/136.

In another embodiment shown in FIG. 2, the second interface 220/236' has a smaller axial width than the first interface 218/236, and, the mid-planes of the interfaces 218/236 and 220/236' are aligned.

In another embodiment shown in FIG. 2, the second interface 320/336' has a smaller axial width than the first interface 318/336, and, the second interface 320/336' is axially juxtaposed above the mid-plane of the first interface 318/336.

In another embodiment shown in FIG. 2, the first interface 418/436 has a smaller axial width than the second interface 420/436', and, the first interface 418/436 is axially juxtaposed above the mid-plane of the second interface 420/436'.

In another embodiment shown in FIG. 2, the first interface 518/536 has a smaller axial width than the second interface 520/536', and, the mid-planes of the interfaces 518/536 and 520/536' are aligned.

In another embodiment shown in FIG. 2, the first interface 618/636 has a smaller axial width than the second interface 620/636', and, the first interface 618/636 is axially juxtaposed below the mid-plane of the second interface 620/636'.

The embodiments of the interfaces 118/136 and 120/136' shown in FIG. 2 and other embodiments may each indicate the API identity and/or dosing concentration. For example, one of the embodiments may indicate that the drug containment device 24 contains nitric oxide at a concentration of 100 ppm, and the collar would require complementary member indexing.

As shown in FIGS. 1, 3, and 4, the valve housing 26 further includes a second end adjacent the interfaces 18/36 and 20/36' and opposite the canister 28. The second end defines a valve outlet 40 that includes an o-ring 41 to seal the valve assembly 13 in some situations, as described below.

As shown in FIGS. 3 and 4, the valve outlet 40 is also in fluid communication with a needle valve 42 disposed within a passageway in the valve housing 26. The needle valve 42 includes an inlet section 43 that threadably connects to the valve housing 26 near the valve inlet 27. The needle valve 42 also includes a movable outlet section 46 that is held in a normally closed position by a compression spring 44. The compression spring 44 forces the outlet section 46 (and, optionally, a seal ring 48) against an internal wall within the valve housing 26 thereby preventing flow between the canister 28 and the valve outlet 40. When the moveable outlet section 46 is in the open position (FIG. 4) the gas from the container can pass through the outlet port 49 and out of the needle valve 42. The seal ring 48 may be constructed from conventional materials, such as rubber or teflon. The needle valve 42 has a co-axial internal passageway where the gas flows out through the center passage outlet.

Figure 7:
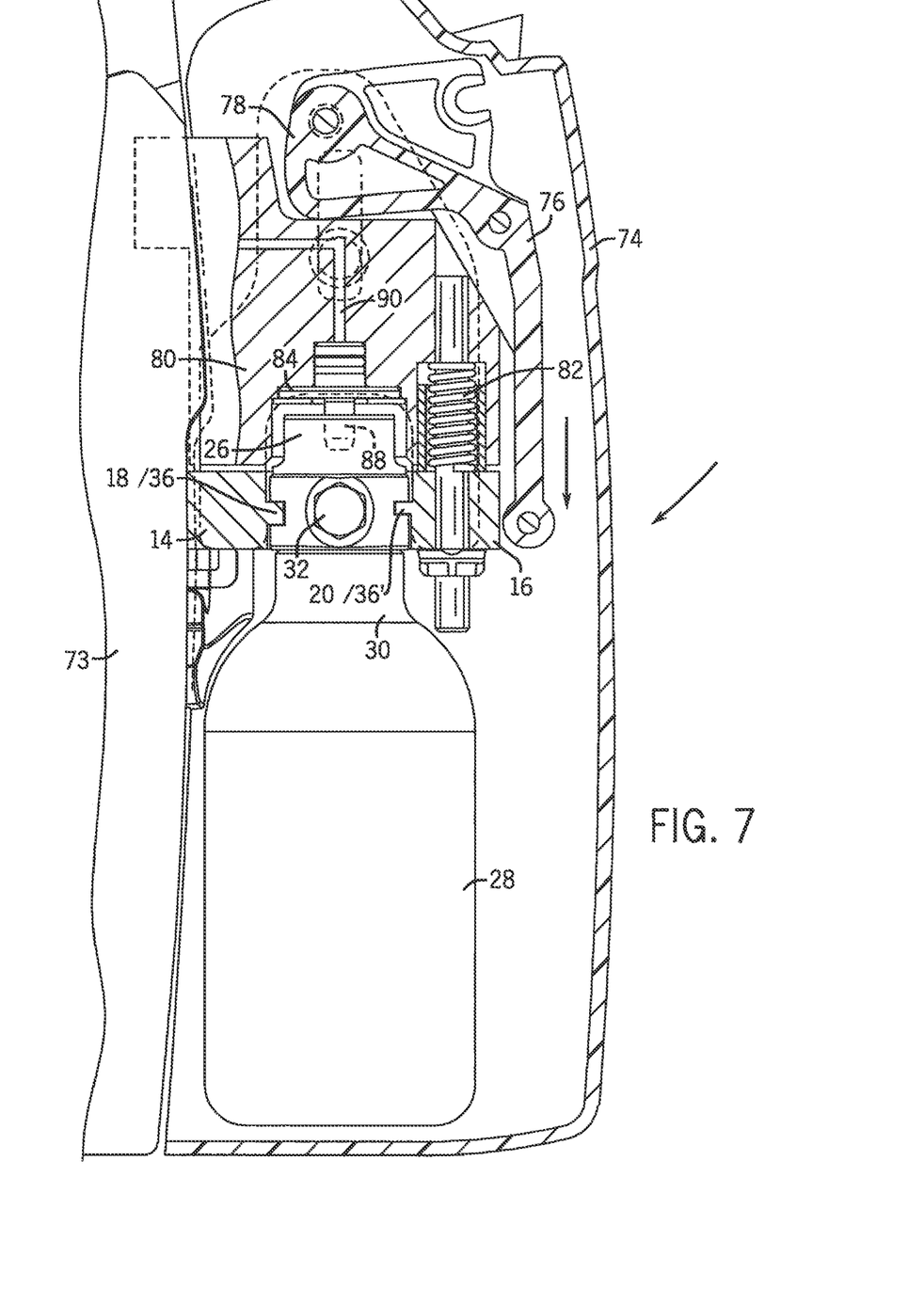

As shown in FIGS. 3, 4 and 7, a valve-receiving assembly 80 includes a receptacle 84 that axially engages the valve housing 26 in the operating position. The receptacle 84 includes side walls 86 that surround the valve housing 26 and ensures good alignment before the valve is engaged. The receptacle 84 also includes an elongated seat 88 that engages the needle valve 42 and forms a seal against the o-ring 41. The seat 88 axially displaces or actuates the needle valve 42 in the operating position. Actuation of the needle valve 42 permits fluid communication between the canister 28 and a receptacle passageway 90 within the seat 88 and the receiving assembly 80. The collar 12 is fixed to a carriage 73.

After actuation, dispensing of the composition from the receptacle passageway 90 and the canister 28 may be controlled by the drug delivery and regulation device 70 and as directed by the keypad 72 and/or an automated program (see FIG. 8). The device 70 may be a corresponding device or any suitable combination of devices and/or components, API or formulations thereof disclosed in U.S. Pat. Nos. 5,885,621; 5,558,083; 5,732,693; 5,752,504; 5,699,790; 5,732,694; 6,089,229; 6,109,260; 6,125,846; 6,164,276; 6,581,592; 5,918,596; 5,839,433; 7,114,510; 5,417,950; 5,670,125; 5,670,127; 5,692,495; 5,514,204; 5,885,621; 6,125,846; and, 7,523,752 as well as U.S. Ser. No. 11/355,670 (US 2007/0190184); Ser. Nos. 11/401,722; 10/053,535; 10/367,277; 10/439,632; and, 10/520,270 (US 2006/0093681), all of which are incorporated herein by reference in their entirety. The associated methods of treatment and drug formulations and dosage forms thereof are also contemplated for use in conjunction with this invention.

Figure 6:
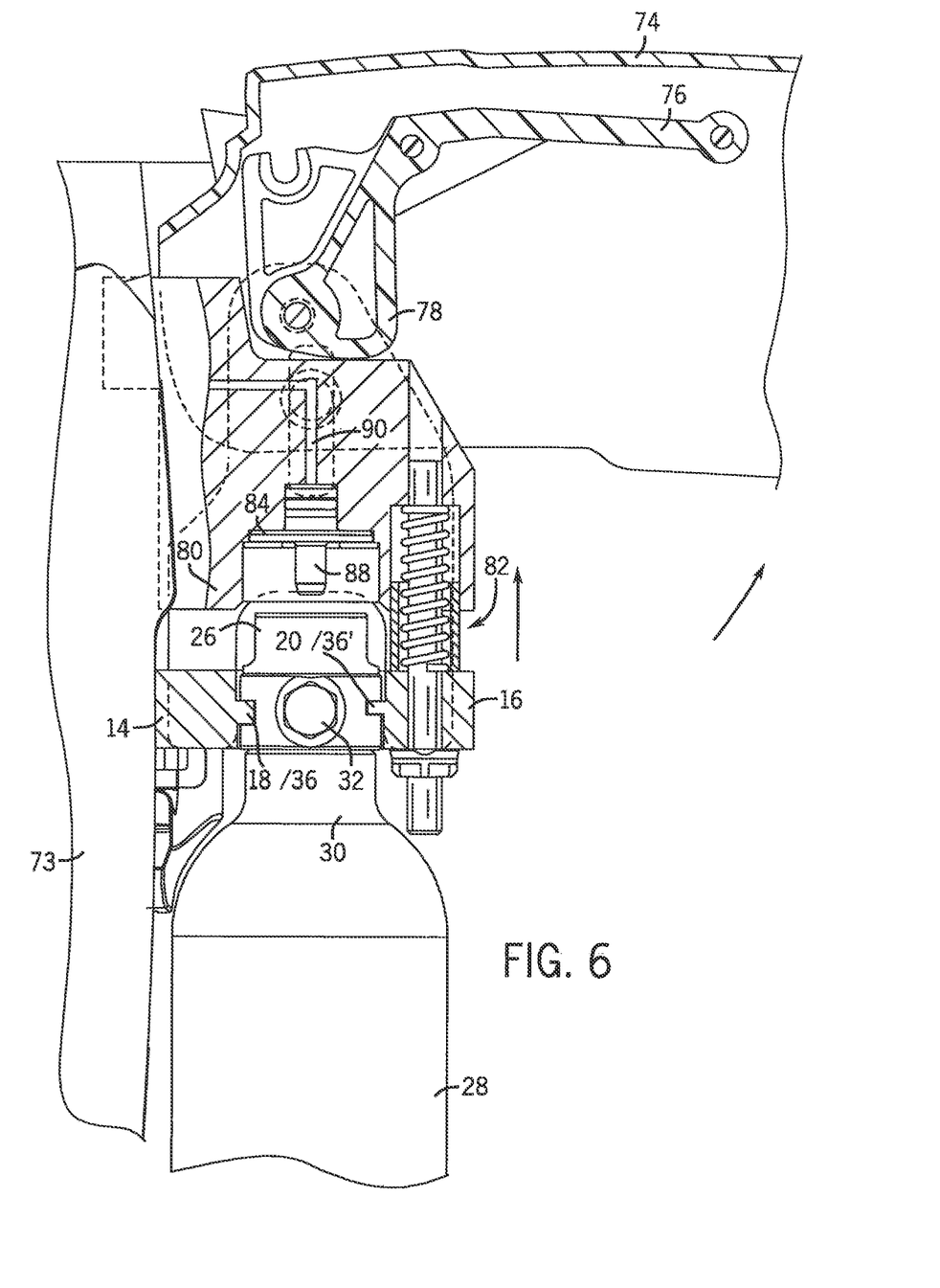

As shown in FIGS. 6-8, the drug delivery and regulation device 70 includes a keypad 72 to permit a user to control and/or program delivery of the API from the canister 28. The pressurized gas drug delivery device 70 also includes a carriage 73 having the collar 12 fixedly mounted thereon. A pivotable cover 74 is fixed to a lever 76. Both the cover 74 and the lever 76 pivot between an open position (see FIG. 6 whereby the indexed drug containment device 24 may be inserted or removed from the collar 12) and an operating/closed position (see FIG. 7 whereby the collar 12 and the device 24 are secured). Once in the operating/closed position, the device 24 is advantageously protected from the exterior environment, which is particularly advantageous in a hospital environment.

As shown in FIGS. 6 and 7, the lever 76 includes a cam surface 78 that moves a valve-receiving assembly 80 to engage the indexed valve assembly 13 in the operating position. In contrast, the receiving assembly 80 is forced upward by a rod/compression spring assembly 82 to disengage the valve assembly 24 in the open position. The lever 76, cam 78, rod/compression spring assembly 82 and carriage 73 make up a plunger assembly for axially actuating the drug containment device 24 into the receptacle 84.

Figure 5:
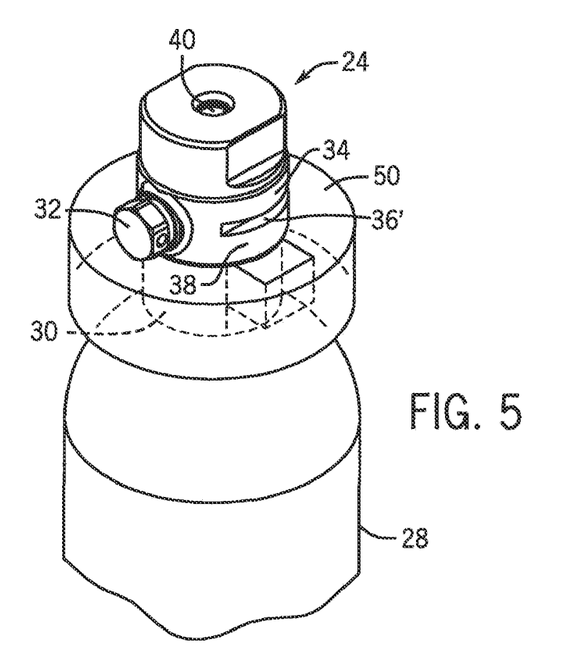
FIG. 5 shows a partial perspective view of the collar canister assembly including a radio frequency identification device.

As shown in FIG. 5, the canister assembly may include a radio frequency identification (RFID) device 50 disposed about the neck 30 of the canister 28. The RFID device 50 transmits a radio frequency to an RFID reader (not shown) disposed within the delivery device to provide further identification features. That is, the RFID reader may be used to determine if appropriate or inappropriate canisters have been inserted.

From the above disclosure it should be apparent that the present invention provides any combination of the following advantages: a linearly actuated canister assembly that can be installed without tools; a device in which a single movement aligns, seals and opens the valve; and indexing of multiple drugs (e.g., nitric oxide, carbon monoxide, and the like).

An exemplary embodiment of the invention has been described in considerable detail. Many modifications and variations to the exemplary embodiment described will be apparent to a person of ordinary skill in the art. Therefore, the invention should not be limited to the embodiment described, but should be defined by the claims that follow.

We claim:

1. A valve assembly comprising:
   a housing and a valve, the valve being disposed within the housing;
   a first indexed member integral to the housing, the first indexed member adapted to be complementary to a second indexed member, wherein the first indexed member comprises a first arcuate opening and a second arcuate opening having at least one of different axial widths or misaligned mid-planes; and
   a radio frequency identification device adapted to communicate with a radio frequency receiver,
   wherein the valve is configured to align with a canister, seal the canister and open in a single movement.

2. The valve assembly of claim 1, wherein the radio frequency identification device is adapted to communicate to the radio frequency receiver identifying information of the contents of a canister that is attachable to the valve.

3. The valve assembly of claim 1, wherein the valve assembly is attachable to a canister comprising an active pharmaceutical ingredient including one of nitric oxide, with a concentration in the range of approximately 50 ppm to 10,000 ppm, carbon monoxide with a concentration in the range of approximately 500 ppm to 20,000 ppm, or, a chalcogenide compound and an inactive carrier gas comprising at least one of $N_2$ and $O_2$.

4. The valve assembly of claim 3, wherein the first and second indexed members are predeterminately adapted to indicate the identity and canister concentration of the active pharmaceutical ingredient.

5. The valve assembly of claim 1, wherein the valve is linearly actuated.

6. A drug containment device comprising:
   a valve assembly comprising a housing and a valve disposed within the housing, a first indexed member integral to the housing, the first indexed member adapted to be complementary to a second indexed member, wherein the first indexed member comprises a first arcuate opening and a second arcuate opening having at least one of different axial widths or misaligned mid-planes,
   a canister in fluid communication with the valve assembly, the canister containing an active pharmaceutical ingredient and,
   wherein the valve is configured to align with the canister, seal the canister and open in a single movement.

7. The drug containment device of claim 6, further comprising a radio frequency identification device adapted to communicate to a radio frequency receiver identifying information of the active pharmaceutical ingredient.

8. The drug containment device of claim 6, wherein the active pharmaceutical ingredient comprises one of nitric oxide, with a concentration in the range of approximately 50 ppm to 10,000 ppm, carbon monoxide with a concentration in the range of approximately 500 ppm to 20,000 ppm, or, a chalcogenide compound and the inactive carrier gas comprises at least one of $N_2$ and $O_2$.

9. The drug containment device of claim 6, wherein the first and second indexed members are predeterminately adapted to indicate the identity and concentration of an active pharmaceutical ingredient.

* * * * *